(12) United States Patent
Bluer et al.

(10) Patent No.: US 10,933,012 B2
(45) Date of Patent: Mar. 2, 2021

(54) SILOXANE COMPOSITION

(71) Applicant: Dow Silicones Corporation, Midland, MI (US)

(72) Inventors: Kristen R. Bluer, Freeland, MI (US); Donald A. Kadlec, Midland, MI (US); John J. Kennan, Midland, MI (US); Kimmai T. Nguyen, Midland, MI (US); Zachary R. Wenzlick, Freeland, MI (US); Fang Zhang, Midland, MI (US)

(73) Assignee: Dow Silicones Corporation, Midland, MI (US)

(*) Notice: Subject to any disclaimer, the term of this patent is extended or adjusted under 35 U.S.C. 154(b) by 148 days.

(21) Appl. No.: 16/084,016

(22) PCT Filed: Nov. 8, 2016

(86) PCT No.: PCT/US2016/060922
§ 371 (c)(1),
(2) Date: Sep. 11, 2018

(87) PCT Pub. No.: WO2017/160349
PCT Pub. Date: Sep. 21, 2017

(65) Prior Publication Data
US 2020/0060962 A1 Feb. 27, 2020

Related U.S. Application Data

(60) Provisional application No. 62/307,718, filed on Mar. 14, 2016.

(51) Int. Cl.
*A61K 8/895* (2006.01)
*A61K 8/81* (2006.01)
*A61K 8/86* (2006.01)
*A61Q 5/00* (2006.01)
*A61Q 19/00* (2006.01)

(52) U.S. Cl.
CPC ............ *A61K 8/895* (2013.01); *A61K 8/8194* (2013.01); *A61K 8/86* (2013.01); *A61Q 5/00* (2013.01); *A61Q 19/00* (2013.01); *A61K 2800/10* (2013.01); *A61K 2800/54* (2013.01); *A61K 2800/592* (2013.01)

(58) Field of Classification Search
CPC ........ A61K 8/895; A61K 8/8194; A61K 8/86; A61K 2800/10; A61K 2800/54; A61K 2800/592; A61K 8/19; A61K 8/585; A61K 8/891; A61Q 5/00; A61Q 19/00; A61Q 19/08
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,296,291 A | 1/1967 | Chalk et al. | |
| 3,516,946 A | 6/1970 | Modic | |
| 3,814,730 A | 6/1974 | Karstedt | |
| 3,928,629 A | 12/1975 | Chandra et al. | |
| 3,989,668 A | 11/1976 | Lee et al. | |
| 4,352,808 A | 10/1982 | Rane et al. | |
| 4,871,782 A | 10/1989 | Modie et al. | |
| 4,970,252 A | 11/1990 | Sakuta et al. | |
| 4,985,459 A | 1/1991 | Sunshine et al. | |
| 4,987,169 A | 1/1991 | Kuwata et al. | |
| 5,036,117 A | 7/1991 | Chung et al. | |
| 5,236,986 A | 8/1993 | Sakuta | |
| 5,741,834 A | 4/1998 | Ward et al. | |
| 5,760,116 A | 6/1998 | Kilgour et al. | |
| 6,162,432 A | 12/2000 | Wallner et al. | |
| 6,355,724 B1 | 3/2002 | LeGrow et al. | |
| 6,605,734 B2 | 8/2003 | Roy et al. | |
| 6,806,339 B2 | 10/2004 | Cray et al. | |
| 6,881,416 B2 | 4/2005 | Fry | |
| 7,172,711 B2 | 2/2007 | Nguyen | |
| 7,517,929 B2 | 4/2009 | Kilgour et al. | |
| 7,592,412 B2 | 9/2009 | Cray et al. | |
| 8,222,364 B2 | 7/2012 | Su et al. | |
| 8,580,285 B2 | 11/2013 | Falk et al. | |
| 8,841,400 B2 | 9/2014 | Henning et al. | |
| 8,946,369 B2 | 2/2015 | Henning et al. | |
| 2009/0171010 A1 | 7/2009 | Kilgour et al. | |
| 2012/0156148 A1 | 6/2012 | Shikano et al. | |
| 2013/0172192 A1 | 7/2013 | Saxena et al. | |
| 2014/0010963 A1 | 1/2014 | Brasseur et al. | |
| 2015/0147286 A1 | 5/2015 | Barrera et al. | |
| 2015/0157724 A1 | 6/2015 | Cauvin et al. | |
| 2015/0190516 A1 | 7/2015 | Cauvin et al. | |

FOREIGN PATENT DOCUMENTS

| | | |
|---|---|---|
| CN | 104448318 A | 3/2015 |
| DE | 102010041887 A1 | 4/2012 |
| EP | 1070734 A2 | 1/2001 |
| JP | 2002179919 A | 6/2002 |
| JP | 2003507551 A | 2/2003 |
| WO | 2001014458 A1 | 3/2001 |
| WO | WO2006058793 A1 | 6/2006 |
| WO | WO2008046763 A1 | 4/2008 |
| WO | WO2008074844 A1 | 6/2008 |
| WO | WO2009042535 A2 | 4/2009 |
| WO | WO2010080755 A1 | 7/2010 |
| WO | WO2011028765 A1 | 3/2011 |
| WO | WO2015117804 A1 | 8/2015 |

OTHER PUBLICATIONS

International Search Report for PCT/US2016/060922 dated Jan. 2, 2017, 4 pages.

(Continued)

*Primary Examiner* — Robert A Wax
*Assistant Examiner* — Quanglong N Truong
(74) *Attorney, Agent, or Firm* — Warner Norcross + Judd LLP

(57) ABSTRACT

A cosmetic composition comprises (A) a silicone elastomer. The (A) silicone elastomer comprises the reaction product of: (a) a branched organosiloxane; (b) a crosslinking agent; and (c) a hydrosilylation catalyst. The cosmetic composition further comprises (B) a carrier fluid. A method of preparing the cosmetic composition is also disclosed.

16 Claims, No Drawings

(56) References Cited

OTHER PUBLICATIONS

English language abstract and machine translation for DE102010041887 (A1) extracted from http://worldwide.espacenet.com database on Aug. 20, 2018, 19 pages.

English language abstract and machine translation for CN104448318 (A) extracted from http://worldwide.espacenet.com database on Aug. 20, 2018, 14 pages.

Asahi Kasei Drum Silicone Technology Libraries, "A Novel Silicone Elastomer Gel Having Both High Film Formability / Sustainability and Smooth Feelings," Sep. 15, 2013, [search on Nov. 17, 2020], Internet URL available at http://www.aws-silicone.com/dcms_media/other/Tech_library3.pdf.

SILOXANE COMPOSITION

CROSS-REFERENCE TO RELATED APPLICATIONS

This application is the National Stage of International Application No. PCT/US2016/060922 filed on 8 Nov. 2016, which claims priority to and all advantages of U.S. Provisional Patent Application No. 62/307,718 filed on 14 Mar. 2016, the content of which is hereby incorporated by reference.

FIELD OF THE INVENTION

The disclosure relates to a cosmetic composition and, more specifically, to a cosmetic composition comprising a silicone elastomer and to its method of preparation.

DESCRIPTION OF THE RELATED ART

Compositions are known in the art and utilized for numerous end use applications and uses. Personal care compositions, for example, are utilized to treat hair, skin, and other parts of the human body. Personal care compositions include various components contingent on a desired end use thereof. Silicone elastomer gels and pastes are examples of components which may be present in personal care compositions.

Silicone elastomer gels and pastes impart desirable properties to a variety of formulations, particularly personal care compositions. They can be used as rheology modifiers or thickeners. In personal care compositions, they are often valued for imparting desirable aesthetics, such as skin feel, to a formulation. They may also be used to deliver actives to a surface. Silicone elastomer gels are typically prepared by crosslinking organopolysiloxanes to form a silicone elastomer in the presence of a swelling solvent. During and/or after the crosslinking step, the swollen silicone elastomer is sheared to create a paste. The paste can be subject to additional processing such as the addition of more solvent, inhibitors, or active ingredients and subject to additional shear to give a uniform paste. Silicone elastomers are commonly dispersed in a volatile silicone carrier fluid to form gelled compositions.

SUMMARY OF THE INVENTION

Disclosed is a cosmetic composition. The cosmetic composition comprises (A) a silicone elastomer. The (A) silicone elastomer comprises the reaction product of: (a) a branched organosiloxane having the following general formula: Si—[[OSiR$_2$]$_c$[OSiR$_2$R$^1$]]$_4$; (b) a crosslinking agent having an average of at least two functional groups R$^2$ reactive with R$^1$ of the (a) branched organosiloxane; and (c) a hydrosilylation catalyst. In the (a) branched organosiloxane, each R independently is R$^1$ or a substituted or unsubstituted hydrocarbyl group, each R$^1$ independently is an unsaturated group or a silicon-bonded hydrogen atom, and each c independently is from 0 to 500. When each R$^1$ independently is an unsaturated group, each R$^2$ is a silicon-bonded hydrogen atom; and when each R$^1$ is a silicon-bonded hydrogen atom, each R$^2$ is an unsaturated group. The cosmetic composition further comprises (B) a carrier fluid.

A method of preparing the cosmetic composition is also disclosed. The method comprises combining the (a) branched organosiloxane; (b) the crosslinking agent having an average of at least two functional groups R$^2$ reactive with R$^1$ of (a) the branched organosiloxane; and (c) a hydrosilylation catalyst. The method also comprises hydrosilylating the (a) branched organosiloxane, the (b) crosslinking agent, and the (c) hydrosilylation catalyst, optionally in the presence of (B) a carrier fluid, to give (A) the silicone elastomer. Finally, the method comprises combining the (A) silicone elastomer with (B) a carrier fluid to give the cosmetic composition.

DETAILED DESCRIPTION OF THE INVENTION

A cosmetic composition and a method of preparing the cosmetic composition are disclosed and described in greater detail below. The cosmetic composition may be prepared based on a particular end use application thereof and may be utilized in diverse end use cosmetic applications. The cosmetic composition is particularly suited for personal care applications, such as treatment methods involving substrates relating to personal care (e.g. hair, skin, teeth, and/or nails).

The cosmetic composition comprises (A) a silicone elastomer. The (A) silicone elastomer comprises the reaction product of (a) a branched organosiloxane; (b) cross-linking agent; and (c) a hydrosilylation catalyst.

Depending on its selection, the (a) branched organosiloxane may be referred to as an organopolysiloxane. Organopolysiloxanes are polymers containing siloxy units independently selected from (R'$_3$SiO$_{1/2}$), (R'$_2$SiO$_{2/2}$), (R'SiO$_{3/2}$), and/or (SiO$_{4/2}$) siloxy units, where R' may be any suitable group or substituent. When R' is a methyl group in siloxy units of an organopolysiloxane, the siloxy units are commonly referred to as M, D, T, and Q units respectively. These siloxy units can be combined in various manners to form cyclic, linear, branched, or resinous structures. The chemical and physical properties of the resulting polymeric structures can vary. For example organopolysiloxanes can be volatile or low viscosity fluids, high viscosity fluids/gums, elastomers or rubbers, and resins. Generally, branching and resinous structures are attributable to the presence of T and/or Q units, and linear polymers consist of repeating D units. The (a) branched organosiloxane may be polymeric, oligomeric, or monomeric.

The (a) branched organosiloxane has the following general formula:

Si—[[OSiR$_2$]$_c$[OSiR$_2$R$^1$]]$_4$ wherein each R independently is R$^1$ or a substituted or unsubstituted hydrocarbyl group, each R$^1$ independently is an unsaturated group or each R$^1$ is a silicon-bonded hydrogen atom, and each c independently is from 0 to 500.

The (a) branched organosiloxane includes a single Q unit and no T units. The (a) branched organosiloxane may optionally include D units, corresponding to each iteration of subscript c. Finally, the (a) branched organosiloxane terminates with an M units. When one or more iteration of subscript c in the general formula is greater than 0, the (a) branched organosiloxane may be referred to as a branched organopolysiloxane. When each iteration of c is insufficiently small to impart polymeric properties, or 0, the (a) branched organosiloxane is generally not referred to as a branched organopolysiloxane, but merely a branched organosiloxane.

Each subscript c is independently selected. As such, the (a) branched organosiloxane may include at least one, alternatively at least two, alternatively at least three, alternatively four, substantially linear, alternatively linear, portions extending from the silicon atom of the Q unit. These substantially linear, alternatively linear, portions correspond to the repeating D units when any iteration of c is greater than 0.

Alternatively, each iteration of c may be 0 such that the (a) branched organosiloxane comprises a Q unit and four M units. In these embodiments, the (a) branched organosiloxane has the general formula Si—[OSiR$_2$R$^1$]]$_4$.

Regardless of the presence or absence of D units in the (a) branched organosiloxane, the (a) branched organosiloxane is a branched organosiloxane, rather than a resin, despite the inclusion of a Q unit. Generally, inclusion of T and/or Q units in a silicone or organopolysiloxane imparts resinous properties associated with three-dimensional networks. However, inclusion of a single Q unit and no T units, as in the (a) branched organosiloxane, does not impart the (a) branched organosiloxane with such a resinous or three-dimensional networked structure. As such, the (a) branched organosiloxane is merely branched (from the single Q unit), but not a resin.

The hydrocarbyl group(s) represented by R may be substituted or unsubstituted, and may be aliphatic, aromatic, cyclic, alicyclic, etc. Moreover, the hydrocarbyl group(s) represented by R may include one or more heteroatoms replacing carbon, e.g. N, S, or O may replace C in the hydrocarbyl group(s) represented by R. The term "substituted" as used in relation to a hydrocarbyl group means, unless indicated otherwise, one or more hydrogen atoms in the hydrocarbyl group has been replaced with another substituent. Examples of such substituents include, for example, halogen atoms; halogen atom containing groups; oxygen atoms; oxygen atom containing groups; nitrogen atoms; nitrogen atom containing groups; sulphur atoms; and sulphur atom containing groups.

Monovalent unsubstituted aliphatic hydrocarbyl groups are exemplified by, but not limited to, alkyl groups, such as methyl, ethyl, propyl, pentyl, octyl, undecyl, and octadecyl and cycloalkyl groups, such as cyclohexyl. Monovalent substituted aliphatic hydrocarbyl groups are exemplified by, but not limited to halogenated alkyl groups such as chloromethyl, 3-chloropropyl, and 3,3,3-trifluoropropyl. Aromatic hydrocarbon groups are exemplified by, but not limited to, phenyl, tolyl, benzyl, styryl, and 2-phenylethyl. Substituted hydrocarbyl groups have one or more hydrogen atoms replaced with another atom or substituent, for example, a halogen atom such as chlorine, fluorine, bromine or iodine, an oxygen atom containing group such as acrylic, methacrylic, alkoxy or carboxyl, a nitrogen atom containing group such as an amino, amido or cyano group, or a sulphur atom containing group such as a mercapto group. Examples of substituted hydrocarbon groups include a propyl group substituted with chlorine or fluorine such as 3,3,3-trifluoropropyl, chlorophenyl, beta-(perfluorobutyl)ethyl or chlorocyclohexyl group. In some embodiments, at least some or all of the R groups are methyl groups.

In a first embodiment, each R$^1$ independently is an unsaturated group. The unsaturated groups represented by R$^1$ may be referred to as ethylenically unsaturated groups or aliphatic unsaturated groups.

The ethylenically unsaturated groups of the (a) branched organosiloxane are located in terminal M units thereof. However, because R may also be R$^1$, the (a) branched organosiloxane may also include pendent ethylenically unsaturated groups. The unsaturated groups represented by R$^1$ may independently comprise a C=C bond, or a C≡C bond. For example, R$^1$ independently may be an alkenyl group and/or an alkynyl group.

When R$^1$ is the unsaturated group, exemplary examples thereof include CH$_2$=CH—, CH$_2$=CHCH$_2$—, CH$_2$=CH(CH$_2$)$_4$—, CH$_2$=C(CH$_3$)CH$_2$—, H$_2$C=C(CH$_3$)—, HC=C(CH$_3$)—, H$_2$C=C(CH$_3$)CH$_2$—, H$_2$C=CHCH$_2$CH$_2$—, H$_2$C=CHCH$_2$CH$_2$CH$_2$—, HC≡C—, HC≡CCH$_2$—, HC≡CCH(CH$_3$)—, HC≡CC(CH$_3$)$_2$—, and HC≡CC(CH$_3$)$_2$CH$_2$—.

In specific embodiments, each R is methyl (Me) and each R$^1$ is vinyl (Vi). In these embodiments, the (a) branched organosiloxane has the general formula:

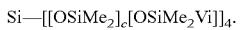

Si—[[OSiMe$_2$]$_c$[OSiMe$_2$Vi]]$_4$.

In a further specific embodiment, each subscript c may be 0. In these embodiments, the (a) branched organosiloxane is merely a single Q unit and four M units, represented by general formula:

Si[OSiMe$_2$Vi]$_4$.

In a second embodiment, each R$^1$ of the (a) branched organosiloxane is a silicon-bonded hydrogen atom. In these embodiments, R is typically free from aliphatic unsaturation, and the (b) branched organosiloxane may be referred to as a branched organohydrogensiloxane.

Because the silicon-bonded hydrogen atoms can be at various locations in addition to terminal locations in the (a) branched organosiloxane, organohydrogensiloxanes suitable for forming the (A) silicone elastomer may comprise any number of (R$_2$SiO$_{2/2}$), (RHSiO$_{2/2}$), (R$_2$HSiO$_{1/2}$), (RH$_2$SiO$_{1/2}$), or other siloxy units.

In a specific embodiment, each R is methyl (Me) and each R$^1$ is silicon-bonded hydrogen. In these embodiments, the (a) branched organosiloxane has the general formula:

Si—[[OSiMe$_2$]$_c$[OSiMe$_2$H]]$_4$.

In a further specific embodiment, each subscript c may be 0. In these embodiments, the (a) branched organosiloxane is merely a single Q unit and four M units, represented by general formula:

Si[OSiMe$_2$H]$_4$.

As introduced above, the (A) silicone elastomer comprises the reaction product of the (a) branched organosiloxane and (b) a crosslinking agent. The (b) crosslinking agent includes at least two functional groups R$^2$. The functional groups R$^2$ of the (b) crosslinking agent are reactive with R$^1$ of the (a) branched organosiloxane. When each R$^1$ of the (a) branched organosiloxane is an unsaturated group, each R$^2$ of the (b) crosslinking agent is a silicon-bonded hydrogen atom. The (a) branched organosiloxane and the (b) crosslinking agent react via hydrosilylation, as described below.

In the first embodiment introduced above, i.e., where each R$^1$ of the (a) branched organosiloxane independently is an unsaturated group, each R$^2$ of the (b) crosslinking agent is a silicon-bonded hydrogen atom. In these embodiments, the (b) crosslinking agent may be referred to as an organosilicon compound, or an organohydrogensiloxane. The (b) crosslinking agent is typically substantially linear, alternatively is linear. However, the (b) crosslinking agent may be cyclic, alicyclic, or have other structures. For example, the (b) crosslinking agent may include at least two cyclosiloxane rings in one molecule. Cyclosiloxane rings contain at least three siloxy units (that is the minimum needed in order to form a siloxane ring), and may be any combination of M, D, T, and/or Q siloxy units that forms a cyclic structure.

In this first embodiment, because the (b) crosslinking agent includes silicon-bonded hydrogen atoms, the (b)

crosslinking agent includes at least one silicon atom. However, the (b) crosslinking agent may be a silicone-organic hybrid, or an organosilicon compound free from siloxane bonds.

In this first embodiment, the (b) crosslinking agent may have the average formula:

$$(R^3{}_2R^2SiO_{1/2})_v(R^3{}_2SiO_{2/2})_x(R^3R^2SiO_{2/2})_y,$$

wherein each $R^2$ is silicon-bonded hydrogen, each $R^3$ independently is a substituted or unsubstituted hydrocarbyl group or $R^2$, and v≥2, x≥0, and y≥2. In specific embodiments, v is from 2 to 10, alternatively from 2 to 8, alternatively from 2 to 6. In these or other embodiments, x is from 0 to 1,000, alternatively from 1 to 500, alternatively from 1 to 200. In these or other embodiments, y is from 2 to 500, alternatively from 2 to 200, alternatively from 2 to 100.

As a specific example in this first embodiment, the (b) crosslinking agent may be selected from a dimethyl, methyl-hydrogen polysiloxane having the average formula;

$$(CH_3)_3SiO[(CH_3)_2SiO]_x[(CH_3)HSiO]_ySi(CH_3)_3$$

where x and y are defined above.

Alternatively or in addition, the (b) crosslinking agent may be an SiH terminal dimethyl polysiloxane having the average formula:

$$H(CH_3)_2SiO[(CH_3)_2SiO]_xSi(CH_3)_2H$$

where x is as defined above. The SiH terminal dimethyl polysiloxane may be utilized alone or in combination with the dimethyl, methyl-hydrogen polysiloxane disclosed immediately above. When a mixture is utilized, the relative amount of each organohydrogensiloxane in the mixture may vary, e.g. such that from 0 to 85, alternatively from 10 to 70, alternatively from 20 to 60, or alternatively 30 to 50, wt % of the total SiH in the mixture is from the SiH content of the terminal dimethyl polysiloxane.

In this first embodiment, the (b) crosslinking agent may be additionally or alternatively be a silicone-organic hybrid. For example, the (b) crosslinking agent may comprise the hydrosilylation reaction product of organopolysiloxanes, in which case the backbone of the (b) crosslinking agent includes organic divalent linking groups associated with the ethylenic unsaturation of one of the organopolysiloxanes. As another example, organohydrogensiloxanes may be reacted with other organopolysiloxanes, or with organic compounds, to give the (b) crosslinking compound having at least two silicon-bonded hydrogen atoms in this first embodiment.

In these embodiments, the (b) crosslinking agent is typically the reaction product of (a1) at least one Si—H compound and (b1) at least one compound having ethylenic unsaturation. Typically, the (a1) Si—H compound and the (b1) compound having ethylenic unsaturation are linear such that the resulting (b) crosslinking agent is also linear. A molar excess of Si—H groups of the (a1) Si—H compound is utilized as compared to the ethylenic unsaturated groups of the (b1) compound such that the (b) crosslinking agent includes the at least two silicon-bonded hydrogen atoms. The reaction product of the (a1) Si—H compound and the (b1) compound having ethylenic unsaturation may be referred to as an (AB)n type copolymer, with the (a1) Si—H compound forming units A and the (b1) compound having ethylenic unsaturation forming units B. Combinations of different (a1) Si—H compounds may be utilized, and combinations of different (b1) compounds having ethylenic unsaturation may be utilized, such that the resulting (b) crosslinking agent comprises distinct units but may not be an ABn type copolymer. The distinct units may be randomized or in block form.

Examples of the (a1) Si—H compound include but are not limited to any of those described above. For example, the (a1) Si—H compound may be an SiH terminal dimethyl polysiloxane and/or a dimethyl, methyl-hydrogen polysiloxane.

The (b1) compound having ethylenic unsaturation may be an organosiloxane or an organic compound. For example, any of the silicon-bonded hydrogen atoms of the SiH terminal dimethyl polysiloxane and/or the dimethyl, methyl-hydrogen polysiloxane may be replaced with unsaturated groups. In these embodiments, the (b1) compound having ethylenic unsaturation may be a silicon-bonded alkenyl terminal dimethyl polysiloxane and/or a dimethyl, methyl-alkenyl polysiloxane. These are merely exemplary examples, and the recited methyl groups may be replaced by other substituted or nonsubstituted hydrocarbyl groups or other substituents, as understood in the art.

In specific embodiments, the (b1) compound has the formula $R^4$—Z—$R^4$, which may be considered as being a "organic", "hydrocarbon", "organic polymer", "polyether" or "organic-siloxane", or combinations thereof, depending on the selection of Z. Z may be a divalent hydrocarbon, a polyoxyalkylene, a polyalkylene, a polyisoalkylene, a hydrocarbon-silicone copolymer, a siloxane, or mixtures thereof. For clarity and ease of reference, all such examples are within the scope of the (b1) compound. $R^4$ independently is a monovalent unsaturated aliphatic hydrocarbon group containing 2 to 12 carbon atoms.

In one embodiment of the (b1) compound, Z is a divalent hydrocarbon. The divalent hydrocarbon Z may contain 1 to 30 carbons, either as aliphatic or aromatic structures, and may be branched or unbranched. Alternatively, the linking group Z may be an alkylene group containing 1 to 12 carbons. In these embodiments, the (b1) compound may be selected from α, ω-unsaturated hydrocarbons.

For example, the (b1) compound may be any diene, diyne or ene-yne compound. With reference to the formula above, in these embodiments, $R^4$ may be, for example, independently selected from $CH_2=CH-$, $CH_2=CHCH_2-$, $CH_2=CH(CH_2)_4-$, $CH_2=C(CH_3)CH_2-$ or and similar substituted unsaturated groups such as $H_2C=C(CH_3)-$, and $HC=C(CH_3)-$. In such embodiments, the (b1) compound may be referred to as an α,ω-unsaturated hydrocarbon. The α,ω-unsaturated hydrocarbon may be, for example, an α,ω-diene of the formula $CH_2=CH(CH_2)_bCH=CH_2$, an α,ω-diyne of the formula $CH\equiv C(CH_2)_bC\equiv CH$, an α,ω-eneyne of the formula $CH_2=CH(CH_2)_bC\equiv CH$, or mixtures thereof, where b is independently from 0 to 20.

Specific examples of suitable diene, diyne or ene-yne compounds include 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

In another embodiment, the (b1) compound is a polyether. In these embodiments, the (b1) compound comprises a polyoxyalkylene group having the formula $(C_mH_{2m}O)$, wherein m is from 2 to 4 inclusive. With reference to the general formula above, Z is the polyoxyalkylene group. In these embodiments, the (b1) compound may be referred to as the polyoxyalkylene.

The polyoxyalkylene may comprise oxyethylene units $(C_2H_4O)$, oxypropylene units $(C_3H_6O)$, oxybutylene or oxytetramethylene units $(C_4H_8O)$, or mixtures thereof, which may be in block form or randomized in the (b) organic compound.

The polyoxyalkylene may have the following general formula:

$$R^4O—[(C_2H_4O)_{c'}(C_3H_6O)_{d'}(C_4H_8O)_{e'}]—R^4$$

wherein each $R^4$ independently is a monovalent unsaturated aliphatic hydrocarbon group containing 2 to 12 carbon atoms, c' is from 0 to 200, d' is from 0 to 200, and e' is from 0 to 200, with the proviso that c', d' and e' are not simultaneously 0. In specific embodiments, c' is from 0 to 50, alternatively from 0 to 10, alternatively from 0 to 2. In these or other embodiments, d' is from 0 to 100, alternatively 1 to 100, alternatively 5 to 50. In these or other embodiments, e' is from 0 to 100, alternatively 0 to 50, alternatively 0 to 30. In various embodiments, the ratio of (d'+e')/(c'+d'+e') is greater than 0.5, alternatively greater than 0.8, or alternatively greater than 0.95.

This polyoxyalkylene is terminated at each molecular chain end (i.e. alpha and omega positions) with $R^4$, which is independently selected and described above. Additional examples of $R^4$ include $H_2C=C(CH_3)CH_2—$, $HC=CHCH_2CH_2—$, $H_2C=CHCH_2CH_2CH_2—$, and $H_2C=CHCH_2CH_2CH_2CH_2—$, $HC\equiv C—$, $HC\equiv CCH_2—$, $HC\equiv CCH(CH_3)—$, $HC\equiv CC(CH_3)_2—$, $HC\equiv CC(CH_3)_2CH_2—$. However, the polyoxyalkylene set forth above is merely one exemplary example of a suitable polyoxyalkylene.

In specific embodiments, the polyoxyalkylene group comprises only oxypropylene units ($C_3H_6O$). Representative, non-limiting examples of polyoxypropylene-containing polyoxyalkylenes include:

$H_2C=CHCH_2[C_3H_6O]_{d'}CH_2CH=CH_2$, $H_2C=CH[C_3H_6O]_{d'}CH=CH_2$, $H_2C=C(CH_3)CH_2[C_3H_6O]_{d'}CH_2C(CH_3)=CH_2$, $HC\equiv CCH_2[C_3H_6O]_{d'}CH_2C\equiv CH$, $HC\equiv CC(CH_3)_2[C_3H_6O]_{d'}C(CH_3)_2C\equiv CH$, where d' is as defined above.

Representative, non-limiting examples of polyoxybutylene or poly(oxytetramethylene) containing polyoxyalkylenes include:

$H_2C=CHCH_2[C_4H_8O]_{e'}CH_2CH=CH_2$ $H_2C=CH[C_4H_8O]_{e'}CH=CH_2$ $H_2C=C(CH_3)CH_2[C_4H_8O]_{e'}CH_2C(CH_3)=CH_2$ $HC\equiv CCH_2[C_4H_8O]e'CH2C\equiv CH$ $HC\equiv CC(CH_3)_2[C_4H_8O]_{e'}C(CH_3)_2C\equiv CH$, where e' is as defined above.

The polyoxyalkylene may be prepared by, for example, the polymerization of ethylene oxide, propylene oxide, butylene oxide, 1,2-epoxyhexane, 1,2-epoxyoctance, and/or cyclic epoxides, such as cyclohexene oxide or exo-2,3-epoxynorborane. The polyoxyalkylene moiety of the polyoxyalkylene may comprise oxyethylene units ($C_2H_4O$), oxypropylene units ($C_3H_6O$), oxybutylene units ($C_4H_8O$), or mixtures thereof. Typically, the polyoxyalkylene group comprises a majority of oxypropylene or oxybutylene units, as defined on a molar basis and indicated in the above formula by the c', d', and e' subscripts.

Polyoxyalkylenes having an unsaturated aliphatic hydrocarbon group at each molecular terminal are commercially available from numerous suppliers.

In another embodiment, Z of the general formula $R^4—Z—R^4$ of the (b1) compound comprises a polyalkylene group. The polyalkylene group may comprise from $C_2$ to $C_6$ alkylene units or their isomers. One specific example is polyisobutylene group, which is a polymer including isobutylene units. For example, the (b1) compound may be a di-allyl terminated polyisobutylene. The molecular weight of the polyisobutylene group may vary, but typically ranges from 100 to 10,000 g/mole.

When the (b) crosslinking agent comprises the reaction product of the (a1) Si—H compound and the (b1) compound having ethylenic unsaturation, the (b) crosslinking agent may be formed along with and/or immediately prior to the (A) silicone elastomer. Alternatively, the (b) crosslinking agent may be first or discretely formed.

In the second embodiment introduced above, i.e., where each $R^1$ of the (a) branched organosiloxane independently is a silicon-bonded hydrogen atom, each $R^2$ of the (b) crosslinking agent is the unsaturated group. In this second embodiment, the (b) crosslinking agent includes at least two unsaturated groups. As such, in this second embodiment, the (b) crosslinking agent may optionally include at least one silicon atom, but may be free from silicon atoms. In these embodiments, the (b1) crosslinking agent may be referred to as an organosilicon compound, an organosiloxane, an organopolysiloxane, or an organic compound.

In this first embodiment, the (b) crosslinking agent may have the average formula:

$$(R^5_2R^4SiO_{1/2})_{v'}(R^5_2SiO_{2/2})_{x'}(R^5R^4SiO_{2/2})_{y'},$$

wherein each $R^5$ is independently a substituted or unsubstituted hydrocarbyl group or $R^4$, each $R^4$ is defined above (as an independently selected unsaturated group), and v'≥2, x'≥0, and y'≥2. In specific embodiments, v' is from 2 to 10, alternatively from 2 to 8, alternatively from 2 to 6. In these or other embodiments, x' is from 0 to 1,000, alternatively from 1 to 500, alternatively from 1 to 200. In these or other embodiments, y' is from 2 to 500, alternatively from 2 to 200, alternatively from 2 to 100. This embodiment of the (b) crosslinking agent is an organopolysiloxane.

As a specific example in this second embodiment, the (b) crosslinking agent may be selected from a dimethyl, methylvinyl polysiloxane having the average formula;

$$(CH_3)_3SiO[(CH_3)_2SiO]_x[(CH_3)ViSiO]_ySi(CH_3)_3$$

where x and y are defined above, and Vi indicates a vinyl group. Any methyl group may be replaced with vinyl, methyl may be replaced with any substituted or unsubstituted hydrocarbyl group, and vinyl may be replaced with any ethylenically unsaturated group. However, this is a typical structure associated with pendent functionality in view of desired crosslink density of the (A) silicone elastomer.

Alternatively or in addition in this second embodiment, the (b1) crosslinking agent may be a dimethyl polysiloxane terminated with silicon-bonded vinyl groups, having the average formula:

$$Vi(CH_3)_2SiO[(CH_3)_2SiO]_xSi(CH_3)_2Vi$$

where x' and Vi is as defined above. The dimethyl polysiloxane terminated with silicon-bonded vinyl groups may be utilized alone or in combination with the dimethyl, methylvinyl polysiloxane disclosed immediately above. When a mixture is utilized, the relative amount of each organopolysiloxane in the mixture may vary, e.g. such that from 0 to 85, alternatively from 10 to 70, alternatively from 20 to 60, or alternatively 30 to 50, wt % of the total vinyl in the mixture is from the vinyl content of the dimethyl polysiloxane terminated with silicon-bonded vinyl groups. Any methyl group may be replaced with vinyl, methyl may be replaced with any substituted or unsubstituted hydrocarbyl group, and vinyl may be replaced with any ethylenically unsaturated group. However, this is a typical structure associated with terminal functionality in view of desired crosslink density of the (A) silicone elastomer.

In this second embodiment, the (b) crosslinking agent may additionally or alternatively be a silicone-organic hybrid. For example, the (b) crosslinking agent may comprise the hydrosilylation reaction product of organopolysiloxanes, in which case the backbone of the (b) crosslinking agent includes organic divalent linking groups associated with the ethylenic unsaturation of one of the organopolysiloxanes. As another example, organohydrogensiloxanes may be reacted with other organopolysiloxanes, or with organic compounds, to give the (b) crosslinking agent having at least two unsaturated groups in this second embodiment.

In the first embodiment described above, the (b) crosslinking agent may be the reaction product of (a1) at least one Si—H compound and (b1) at least one compound having ethylenic unsaturation. In that first embodiment, a molar excess of Si—H groups of the (a1) Si—H compound is utilized as compared to the ethylenic unsaturated groups of the (b1) compound such that the (b) crosslinking agent includes the at least two silicon-bonded hydrogen atoms. In this second embodiment, the (b) crosslinking agent may also be the reaction product of (a1) at least one Si—H compound and (b1) at least one compound having ethylenic unsaturation. However, in this second embodiment, a molar excess of ethylenic unsaturated groups of the (b1) compound are utilized as compared to Si—H groups of the (a1) Si—H compound such that the (b) crosslinking agent includes the at least two unsaturated groups.

The reaction product of the (a1) Si—H compound and the (b1) compound having ethylenic unsaturation may be referred to as an (AB)n type copolymer, with the (a1) Si—H compound forming units A and the (b1) compound having ethylenic unsaturation forming units B. Combinations of different (a1) Si—H compounds may be utilized, and combinations of different (b1) compounds having ethylenic unsaturation may be utilized, such that the resulting (b) crosslinking agent comprises distinct units but may not be an ABn type copolymer. The distinct units may be randomized or in block form.

Examples of the (a1) Si—H compound include but are not limited to any of those described above. For example, the (a1) Si—H compound may be an SiH terminal dimethyl polysiloxane and/or a dimethyl, methyl-hydrogen polysiloxane.

The (b1) compound having ethylenic unsaturation may also be any of those described above, whether an organopolysiloxane, an organic compound, a silicon-organic hybrid, etc. As such, the (a1) Si—H compound and the (b1) compound having ethylenic unsaturation may be selected from those same compounds described above, subject to the reaction product (i.e., the (b) crosslinking agent) having at least two unsaturated groups in this second embodiment.

Alternatively or in addition, in this second embodiment, the (b) crosslinking agent may itself be any of the (b1) compounds described above, e.g. without first forming the (b) crosslinking agent by reacting the (b1) compound with the (a1) Si—H compound. For example, the (b) crosslinking agent may be an unsaturated hydrocarbon.

Regardless of the particular embodiment, the (a) branched organosiloxane may comprise a combination or two or more different branched organosiloxanes in concert, and the (b) crosslinking agent may comprise two or more different crosslinking agents in concert. The (a) branched organosiloxane and the (b) crosslinking agent react in the presence of (c) a hydrosilylation catalyst to give the (A) silicone elastomer.

The (c) hydrosilylation catalyst may be any catalyst typically employed for hydrosilylation reactions. In certain embodiments, the (c) hydrosilylation catalyst comprises a platinum group metal-containing catalyst. By platinum group it is meant ruthenium, rhodium, palladium, osmium, iridium and platinum as well as any complexes thereof. Platinum group metal-containing catalysts useful for the (c) hydrosilylation catalyst include the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296.291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum group-containing catalyst can be platinum group metal, platinum group metal deposited on a carrier such as silica gel or powdered charcoal, or a compound or complex of a platinum group metal. Specific examples of platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in Roy, U.S. Pat. No. 6,605,734. These alkene-platinum-silyl complexes may be prepared, for example by mixing 0.015 mole (COD)$PtCl_2$ with 0.045 mole COD and 0.0612 moles $HMeSiCl_2$.

The relative amounts of the (a) branched organosiloxane and the (b) crosslinking agent will depend on the selection of the individual components and the desired SiH to aliphatic unsaturation ratio. The molar ratio of SiH to unsaturated groups to prepare the (A) silicone elastomer may range from 10:1 to 1:10, alternatively 5:1 to 1:5, or alternatively 4:1 to 1:4.

If desired, the (A) silicone elastomer may be formed in the presence of additional monomers or compounds, which may be reactive with the (a) branched organosiloxane and/or the (b) crosslinking agent. For example, the additional monomers or compounds may be incorporated into the (A) silicone elastomer as pendent groups, which may be utilized to selectively modify properties of the (A) silicone elastomer. Specific examples of such compounds include hydrocarbons having one terminal unsaturated aliphatic group, e.g. alpha olefins such as 1-hexene, 1-octene, 1-decene, 1-undecene, 1-decadecene, and similar homologs; aryl containing hydrocarbons, such as alpha methyl styrene; or a polyoxyalkylene having only one terminal aliphatic unsaturated group.

The (A) silicone elastomer may also be formed in the presence of a silicone polyether polymer, as disclosed in copending application Ser. No. 62/307,678, which is filed herewith and incorporated by reference herein in its entirety.

The cosmetic composition also includes (B) a carrier fluid. The (A) silicone elastomer may be prepared in the (B) carrier fluid, or the (A) silicone elastomer may be combined with the (B) carrier fluid after being prepared or at any stage of its preparation. The (A) silicone elastomer may be prepared in the presence of the (B) carrier fluid and then combined If the hydrosilylation reaction to prepare the (A) silicone elastomer is carried out in a solvent or carrier, the solvent or carrier may serve as the (B) carrier fluid for the cosmetic composition. The carrier fluid may solubilize, alternatively partially solubilize, the (A) silicone elastomer.

Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the (B) carrier fluid is an organic liquid. Organic liquids include those considered oils or solvents. The organic liquids are exemplified by, but not limited to, aromatic hydrocarbons, aliphatic hydrocarbons, alcohols having more than 6 carbon atoms, aldehydes, ketones, amines, esters, ethers, glycols, glycol ethers, alkyl halides and aromatic halides. Hydrocarbons include, isododecane, isohexadecane, Isopar L (C11-C13), Isopar H(C11-C12), hydrogentated polydecene. Ethers and esters include, isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic carrier fluids suitable as a stand-alone compound or as an ingredient to the carrier fluid include fats, oils, fatty acids, and fatty alcohols.

The (B) carrier fluid may also be a low viscosity organopolysiloxane or a volatile methyl siloxane or a volatile ethyl siloxane or a volatile methyl ethyl siloxane having a viscosity at 25° C. in the range of 1 to 1,000 mm$^2$/sec, such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3, bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, caprylyl methicone, and any mixtures thereof.

The amount of the (B) carrier fluid in the cosmetic composition may vary. In certain embodiments, the cosmetic composition comprises the (B) carrier fluid in an amount of from 0 to 98 weight percent, alternatively 0.5 to 90 weight percent, alternatively 5 to 80 weight percent, based on the total weight of the cosmetic composition.

In certain embodiments, the cosmetic composition further comprises (C) a personal care ingredient, which may be selected based on the desired end use application of the cosmetic composition.

The (C) personal care ingredient may be a liquid, a solid, an encapsulated liquid, etc. Various examples of the (C) personal care ingredient are described below. Any of these personal care ingredients, or a combination of two or more different personal care ingredients, may be utilized as the (C) personal care ingredient. For clarity and consistency, "the (C) personal care ingredient" encompasses embodiments where the cosmetic composition includes but one or two or more personal care ingredients.

In certain embodiments, the (C) personal care ingredient comprises a skin care ingredient. In these embodiments, the cosmetic composition may be referred to as a skin care composition. If utilized to prepare the cosmetic composition, the skin care ingredient is typically selected from water phase stabilizing agents, cosmetic biocides, conditioning agents (which may be silicone, cationic, hydrophobic, etc.), emollients, moisturizers, colorants, dyes, ultraviolet (UV) absorbers, sunscreen agents, antiperspirants, antioxidants, fragrances, antimicrobial agents, antibacterial agents, antifungal agents, antiaging actives, anti-acne agents, skin-lightening agents, pigments, preservatives, pH controlling agents, electrolytes, chelating agents, plant extracts, botanical extracts, sebum absorbents, sebum control agents, vitamins, waxes, surfactants, detergents, emulsifiers, thickeners, propellant gases, skin protectants, film forming polymers, light scattering agents, and combinations thereof. With some of these skin care embodiments, the cosmetic composition may be referred to as a sunscreen, a shower gel, a soap, a hydrogel, a cream, a lotion, a balm, foundation, lipstick, eyeliner, a cuticle coat, or blush. Various species of such skin care ingredients are known by one of ordinary skill in the art.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as $C_{30-45}$ alkyl methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched $C_8$-$C_{16}$ esters; isohexyl neopentanoate; ester oils such as isononyl isononanoate, cetostearyl octanoate, isopropyl myristate, palmitate derivatives (e.g. dextrin palmitate), stearates derivatives, diisostearyl malate, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Examples of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30-45}$ alkyldimethylsilyl polypropylsilsesquioxane), stearyl dimethicone, alkylmethylsiloxanes including long-chain alkyl groups in alkylmethylsiloxy units, and mixtures thereof.

Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of surface active materials may be anionic, cationic or non ionic, and include organomodified silicones such as dimethicone copolyol; oxyethylenated and/or oxypropylenated ethers of glycerol; oxyethylenated and/or oxypropylenated ethers of fatty alcohols such as ceteareth-30, $C_{12-15}$ pareth-7; fatty acid esters of polyethylene glycol such as PEG-50 stearate, PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates such as disodium PEG-5 citrate lauryl sulphosuccinate and disodium ricinoleamido MEA sulphosuccinate; alkyl ether sulphates, such as sodium lauryl ether sulphate; isethionates; acylglutamates, such as disodium hydrogenated tallow glutamate; alkyl polyglucosides (e.g. decyl glucoside); betaine derivatives; and mixtures thereof.

Further examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Nonionic surfactants include condensates of ethylene oxide with long chain fatty alcohols or fatty acids such as a C12-16 alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, and fatty amine oxides, dimethicone copolyols, fatty acid esters of polyols, for instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers, polysorbate 80, sorbitan sesquioleate, and glyceryl stearate.

Anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates, carboxylates (sodium 2-(2-hydroxyalkyloxy)acetate)), amino acid derivatives (N-acylglutamates, N-acylgly-cinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), fatty acid soaps, fatty acid salts (e.g. C6-C30 fatty acid salts) (including those derived from amines, e.g. triethanolamine stearate) and mixtures thereof.

Amphoteric and zwitterionic surfactants include imidazoline compounds, alkylamino acid salts, betaines, N-alkylamidobetaines and derivatives thereof, proteins and derivatives thereof, glycine derivatives, sultaines, alkyl polyaminocarboxylates and alkylamphoacetates, N-acylamino acids (such as N-alkylaminoacetate and disodium cocoamphodiacetate), amine oxides (such as stearamine oxide), amphoteric silicone surfactants (such as dimethicone copolyol phosphates), and mixtures thereof.

Cationic surfactants include alkylamine salts, quaternary ammonium salts, sulphonium salts, and phosphonium salts.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxyethylcellulose, hydroxypropylcellulose, polypropylhydroxyethylcellulose), starch and starch derivatives (such as hydroxyethylamylose and starch amylase), polyoxyethylene, carbomer, alginates (such as sodium alginate), arabic gum, cassia gum, carob gum, scleroglucan gum, gellan gum, rhamsan gum, karaya gum, carrageenan gum, guar gum and guar gum derivatives, cocamide derivatives (including cocamidopropyl betaine and cocamide MIPA), alkyl alcohols (such as cetearyl alcohol, stearyl alcohol, and other fatty alcohols), gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives (e.g. methylparaben, propylparaben), hydantoin derivatives, chlorhexidine and its derivatives, imidazolidinyl urea, diazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, methylchloroisothiazolinone, methylisothiazolinone, and mixtures thereof.

Examples of sebum absorbants or sebum control agents include silica silylate, silica dimethyl silylate, dimethicone/vinyl dimethicone crosspolymer, polymethyl methacrylate, cross-linked methylmethacrylate, aluminum starch octenylsuccinate, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc, and mixtures thereof. Surface treatments include those treatments based on lecithin, silicone, silanes, fluoro compounds, and mixtures thereof.

Examples of silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats, e.g. Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethylhexyl methoxycinnamate (or octyl methoxycinnamate), octyl salicylate (or ethylhexyl salicylate), oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl triaminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, octyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants include allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; Haematoxylon brasiletto wood extract; HC dyes; Lawsonia inermis (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl $C_{21}$-$C_{22}$ isoalkyl acidate; isatin; Isatis tinctoria leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; 1,2,4-trihydroxybenzene.

Examples of fragrances include perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Deiphone, Muscone, Neobutenone, Plicatone, Veloutone, 2,4,4,7-Tetramethyl-oct-6-en-3-one, and Tetrameran. The fragrance may be derived or extracted from flowers, seeds, leaves, and/or roots of plants, seaweed, etc. The fragrance may be extracted from an animal, e.g. from a secretion gland, and may be a musk or sperm oil. The fragrance may also be artificially synthesized, e.g. menthol, acetate, vanilla, etc.

In specific embodiments, the perfume ketones are selected for odor character from Alpha Damascone, Delta Damascone, iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

In specific embodiments, the perfume aldehyde is selected for odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl) oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3) (4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carbox aldehyde, 5 or 6 methoxy 10 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, Camellia sinensis oil, chitosan ascorbate, chitosan glycolate, chitosan salicylate, chlorogenic acids, cysteine, cysteine HCl, decyl mercaptomethyl imidazole, erythorbic acid, diamylhydroquinone, di-t-butyl-hydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (Melaleuca aftemifolia) oil, tocopheryl acetate, tetrahexyldecyl ascorbate, tetrahydrodiferuloyl-methane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

In a specific embodiment, the cosmetic composition is a sunscreen. In these embodiments, personal care ingredient comprises the sunscreen agent. The sunscreen agent may be, for example, a sunscreen additive, an SPF booster, a photostabilizer, a film-forming polymer, etc. The sunscreen may be also or alternatively be utilized in sunless tanning applications. Specific examples of sunscreen agents are set forth above.

In other embodiments, the (C) personal care ingredient comprises a hair care ingredient. In these embodiments, the cosmetic composition may be referred to as a hair care composition. If utilized to prepare the cosmetic composition, the hair care ingredient is typically selected from conditioning agents (which may be silicone, cationic, hydrophobic, etc.), colorants, dyes, ultraviolet (UV) absorbers, preservatives, plant extracts, fatty alcohols, vitamins, fragrance, anti-dandruff agents, color care additives, pearlising agents, pH controlling agents, electrolytes, chelating agents, styling agents, ceramides, amino-acid derivatives, suspending agents, surfactants, detergents, emulsifiers, thickeners, oxidizing agents, reducing agents, film-forming polymers, and combinations thereof. With some of these hair care embodiments, the cosmetic composition may be referred to as a shampoo, a rinse-off conditioner, a leave-in conditioner, a gel, a pomade, a serum, a spray, a coloring product, or mascara. Examples of many of these hair care ingredients are set forth above as suitable personal care ingredients.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of antidandruff agents include pyridinethione salts, selenium compounds such as selenium disulfide, and soluble antidandruff agents, and mixtures thereof.

In other embodiments, the (C) personal care ingredient comprises a nail care ingredient. In these embodiments, the cosmetic composition may be referred to as a nail care composition. If utilized to prepare the cosmetic composition, the nail care ingredient may be any ingredient utilized in nail care compositions, e.g. nail polishes, nail gels, nail tips, acrylic finishes, etc. Examples of such nail care ingredients include pigments, resins, solvents, volatile halogenated compounds (e.g. methoxynonafluorobutane and/or ethoxynonafluorobutane), etc.

More specifically, examples of nail care ingredients include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; Cetraria islandica extract; Chondrus crispus; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

In other embodiments, the (C) personal care ingredient comprises a tooth care ingredient. In these embodiments, the cosmetic composition may be referred to as a tooth care composition. One specific example of such a tooth care composition is toothpaste. Another example of a tooth care composition is a tooth whitening composition. The tooth care ingredient may be any tooth care ingredient suitable for the tooth care composition, such as an abrasive compound (e.g. aluminum hydroxide, calcium carbonate, silica, zeolite), a fluoride compound, a surfactant, a flavorant, a remineralizer, an antibacterial agent, etc.

In certain embodiments, the (C) personal care ingredient comprises a film-forming polymer, which may be utilized as the (C) personal care ingredient whether the cosmetic composition is utilized for skin care, hair care, etc. "Film-forming polymer," as used herein, means a polymer or oligomer which is capable of, by itself or optionally in the presence of a film-forming agent, forming a film on a substrate. The film-forming polymer may form the film upon an application of a curing condition, e.g. the application of heat, exposure to atmospheric conditions, etc. Alternatively, the film-forming polymer may form the film upon evaporation of any carrier vehicle in which the film-forming polymer may optionally be disposed. The film-forming polymer may undergo a reaction, e.g. the film-forming polymer may become cross-linked or otherwise include additional bonds, when forming the film. However, the film-forming polymer may form the film in the absence of such a reaction. The film-forming polymer may be a gelling agent. The film-forming polymer is particularly advantageous when the cosmetic composition is the sunscreen, although the (C) personal care ingredient may comprise the film-forming polymer in other compositions as well.

The substrate on which the film is formed may be any substrate, although the substrate is generally a portion of a mammal, particularly a human, as described in greater detail below with reference to the treatment method. Specific examples of suitable substrates include skin, hair, and nails.

Generally, the film is continuous, although the film may have a varying thickness. By continuous, it is meant that the film does not define any apertures. The film may be referred to as being macroscopically continuous. The film may be supported by the substrate, or may be bonded, e.g. physically and/or chemically, to the substrate. In certain embodiments, the film is optionally removable from the substrate, e.g. the film may be peelable from the substrate. The film may remain intact as a free-standing film upon being separated from the substrate or may be separated through application of shear, which may damage and/or destroy continuity of the film.

Specific examples of film-forming polymers that are suitable include acrylic polymers, silicone resins (e.g. polypropylsilsesquioxane), polyurethanes, polyurethane-acrylics, polyesters, polyester-polyurethanes, polyether-polyurethanes, polyesteramides, alkyds, polyamides, polyureas, polyurea-polyurethanes, cellulose-based polymers (e.g. nitrocellulose), silicones, acrylic-silicones, polyacrylamides, fluoropolymers, polyisoprenes, and any copolymers or terpolymers thereof or including one of these. The term "silicones," as used herein with reference to suitable film-forming polymers, includes linear, branched, and resinous silicones, although resinous silicones are generally referred to as silicone resins rather than polymers. The silicone may be modified, e.g. the silicone may be a silicone-grafted acrylic polymer.

As introduced above, the film-forming polymer may be disposed in a carrier vehicle, which may partially or fully solubilize the film-forming polymer. Depending on a selection of the film-forming polymer, the carrier vehicle may be, for example, an oil, e.g. an organic oil and/or a silicone oil, a solvent, water, etc. The film-forming polymer may be in the form of polymer particles, which are optionally surface-stabilized with at least one stabilizer, and the polymer particles may be present as a dispersion or emulsion.

The film-forming polymer may be a block polymer, which may be styrene-free. Typically, the block polymer comprises at least one first block and at least one second block, which may be linked together via an intermediate block comprising at least one constituent monomer of the first block and at least one constituent monomer of the second block. Generally, the glass transition temperatures of the first and second blocks are different from one another.

Monomers that may be utilized to prepare the block polymer include, for example, methyl methacrylate, isobutyl (meth)acrylate and isobornyl (meth)acrylate, methyl acrylate, isobutyl acrylate, n-butyl methacrylate, cyclodecyl acrylate, neopentyl acrylate, isodecylacrylamide 2-ethylhexyl acrylate and mixtures thereof.

In specific embodiments, the film-forming polymer be obtained or generated via free-radical polymerization. For example, the film-forming polymer may be generated via free-radical polymerization of at least one acrylic monomer and at least one silicone- or hydrocarbon-based macromonomer including a polymerizable end group.

Specific examples of hydrocarbon-based macromonomers include homopolymers and copolymers of linear or branched $C_8$-$C_{22}$ alkyl acrylate or methacrylate. The polymerizable end group may be a vinyl group or a (meth)acrylate group, e.g. poly(2-ethylhexyl acrylate) macromonomers; poly(dodecyl acrylate) or poly(dodecyl methacrylate) macromonomers; poly(stearyl acrylate) or poly(stearyl methacrylate) macromonomers, etc. Such macromonomers generally include one (meth)acrylate group as the polymerizable end group.

Additional examples of hydrocarbon-based macromonomers include polyolefins containing an ethylenically unsaturated end group (as the polymerizable end group), e.g. a (meth)acrylate end group. Specific examples of such polyolefins include polyethylene macromonomers, polypropylene macromonomers, polyethylene/polypropylene copolymer macromonomers, polyethylene/polybutylene copolymer macromonomers, polyisobutylene macromonomers; polybutadiene macromonomers; polyisoprene macromonomers, polybutadiene macromonomers; and poly (ethylene/butylene)-polyisoprene macromonomers Examples of silicone-based macromonomers include organopolysiloxanes containing the polymerizable end group, e.g. a (meth)acrylate end group. The organopolysiloxane may be linear, branched, partially branched, or resinous. In various embodiments, the organopolysiloxane is linear. In these embodiments, the organopolysiloxane may be polydimethylsiloxane, although hydrocarbon groups other than methyl groups may be present therein along with or in lieu of methyl groups. Typically, the polymerizable end group is terminal, although the polymerizable end group may optionally be pendant. One specific example of a silicone-based macromonomer is a monomethacryloxypropyl polydimethylsiloxane.

In certain embodiments, the film-forming polymer is an organic film-forming polymer that is soluble in oil as the carrier vehicle. In these embodiments, the film-forming polymer may be referred to as a liposoluble polymer. The liposoluble polymer may be of any type and specific examples thereof include those comprising or formed from olefins, cycloolefins, butadiene, isoprene, styrene, vinyl ethers, vinyl esters, vinyl amides, (meth)acrylic acid esters or amides, etc.

In one embodiment, the lipsoluble polymer is formed from monomers selected from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate, stearyl (meth)acrylate, and combinations thereof.

Alternatively still, the liposoluble polymer may be an acrylic-silicone grafted polymer, which typically includes a silicone backbone and acrylic grafts or alternatively includes an acrylic backbone and silicone grafts.

The film-forming polymer may be halogenated, e.g. the film-forming polymer may include fluorine atoms.

Alternatively as introduced above, the film-forming polymer may be a cellulose-based polymer, such as nitrocellulose, cellulose acetate, cellulose acetobutyrate, cellulose acetopropionate or ethylcellulose. Alternatively still, the film-forming polymer may comprise a polyurethane, an acrylic polymer, a vinyl polymer, a polyvinyl butyral, an alkyd resin, or resins derived from aldehyde condensation products, such as arylsulfonamide-formaldehyde resins.

Further, as introduced above, the film-forming polymer may comprise the silicone, which may be linear, branched, or resinous. Resinous silicones generally include at least one T and/or Q unit, as understood in the art. Examples of resinous silicones include silsesquioxanes. The silicone may include any combination of M, D, T, and Q units so long as the silicone constitutes the film-forming polymer.

When the film-forming polymer comprises the silicone, the film-forming polymer may comprise an amphiphilic silicone. Amphiphilic silicones typically contain a silicone portion which is compatible with a silicone medium, and a hydrophilic portion. The hydrophilic portion may be, for example, the residue of a compound selected from alcohols and polyols, having 1 to 12 hydroxyl groups, and polyoxyalkylenes (e.g. those containing oxypropylene units and/or oxyethylene units).

The amphiphilic silicone may be an oil with or without gelling activity. Oils of this kind may comprise, for example, dimethicone copolyols, bis-hydroxyethoxypropyl dimethicone, etc.

In one embodiment, the film-forming polymer comprises a silicone organic elastomer gel. Silicone organic elastomer gels comprise linear organopolysiloxane chains crosslinked via polyoxyalkylenes. The silicone organic elastomer gel may further include hydrophilic polyether functionality pending from the linear organopolysiloxane chains. Specific examples of suitable silicone organic elastomer gels are disclosed in International (PCT) Appln. No. PCT/US2010/020110, which is incorporated by reference herein in its entirety.

Additional examples of cross-linked silicone compounds suitable for use as the film-forming polymer are disclosed in U.S. application Ser. Nos. 10/269,758 and 10/228,890, the contents of which are incorporated by reference herein in their respective entireties. Additional examples of other film-forming polymers suitable for the cosmetic composition are disclosed in International (PCT) Serial Nos. PCT/EP2007/064259, PCT/EP2007/060682, and PCT/EP2005/013018, which are each incorporated by reference herein in their respective entireties.

When the (C) personal care ingredient comprises the film-forming polymer, the film-forming polymer may be present in the cosmetic composition in various amounts, e.g. from greater than 0 to less than 100, alternatively from 0.1 to 60, alternatively from 0.1 to 50 percent by weight based on the total weight of the cosmetic composition. Combinations of different types of film-forming polymers may be utilized.

In various embodiments, the (C) personal care ingredient may comprise or be referred to as a personal care active, a health care active, or combination thereof (collectively "active" or "actives"). As used herein, a "personal care active" means any compound or mixtures of compounds that are known in the art as additives in personal care formulations, typically for providing a cosmetic and/or aesthetic benefit. A "healthcare active" means any compound or mixtures of compounds that are known in the art to provide a pharmaceutical or medical benefit. Thus, "healthcare active" includes materials considered as an active ingredient or active drug ingredient as generally used and defined by the United States Department of Health & Human Services Food and Drug Administration, contained in Title 21, Chapter I, of the Code of Federal Regulations, Parts 200-299 and Parts 300-499. Specific personal care actives and health care actives are described below. These personal care actives and health care actives may constitute the (C) personal care ingredient whether the (C) personal care ingredient is utilized to form, for example, the skin care composition, the hair care composition, the nail care composition, and/or the tooth care composition. For example, in various embodiments, the same personal care ingredient may be utilized to form either the hair care composition or the skin care composition. As understood in the art, at least some of the personal care actives described below are species of certain personal care ingredients introduced above with respect to the skin care composition, the hair care composition, the nail care composition, and the tooth care composition, respectively. For example, numerous species of plant or vegetable extracts are described below, which are exemplary examples of plant extracts set forth above as suitable personal care ingredients. The active ingredients or actives described below may constitute the (C) personal care ingredient of the cosmetic composition or may be utilized in combination therewith.

Useful active ingredients for use in the cosmetic composition include vitamins and vitamin derivatives, including "pro-vitamins". Vitamins useful herein include, but are not limited to, Vitamin A1, retinol, C2-C18 esters of retinol, vitamin E, tocopherol, esters of vitamin E, and mixtures thereof. Retinol includes trans-retinol, 1, 3-cis-retinol, 11-cis-retinol, 9-cis-retinol, and 3,4-didehydro-retinol, Vitamin C and its derivatives, Vitamin B1, Vitamin B2, Pro Vitamin B5, panthenol, Vitamin B6, Vitamin B12, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate. In general, retinol, all trans retinoic acid and derivatives, isomers and analogs thereof, are collectively termed "retinoids".

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active can be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Protease include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. In a specific embodiment, natural papain is utilized as the enzyme. Further, stimulating hormones, e.g. insulin, can be used together with the enzyme(s) to boost effectiveness.

The active may also be one or more plant or vegetable extract. Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric[Curcuma] extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine, Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, Salvia extract, Saponaria extract, Bamboo extract, Crataegus fruit extract, Zanthoxylum fruit extract, shiitake extract, Rehmannia root extract, gromwell extract, Perilla extract, linden extract, Filipendula extract, peony extract, Calamus Root extract, white birch extract. Horsetail extract, Hedera Helix(Ivy) extract, hawthorn extract, Sambucus nigra extract, Achillea millefolium extract, Mentha piperita extract, sage extract, mallow extract, Cnidium officinale Root extract, Japanese green gentian extract, soybean extract, jujube extract, thyme extract, tea extract, clove extract, Gramineae imperata cyrillo extract, Citrus unshiu peel extract Japanese Angellica Root extract, Calendula extract, Peach Kernel extract, Bitter orange peel extract, Houttuyna cordata extract, tomato extract, natto extract, Ginseng extract, Green tea extract (camelliea sinesis), garlic extract, wild rose extract, hibiscus extract, Ophiopogon tuber extract, Nelumbo nucifera extract, parsley extract, honey, hamamelis extract, Parietaria extract, Isodonis herba extract, bisabolol extract, Loquat extract, coltsfoot extract, butterbur extract, Porid cocos wolf extract, extract of butcher's broom, grape extract, propolis extract, luffa extract, safflower extract, peppermint extract, linden tree extract, Paeonia extract, hop extract, pine tree extract, horse chestnut extract, Mizu-bashou [Lysichiton camtschatcese] extract, Mukurossi peel extract, Melissa extract, peach extract, cornflower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, royal jelly extract, and combinations thereof.

Representative, non-limiting examples of healthcare actives useful as drugs in the present compositions are described below. One or more of the drugs can be used, either alone or in combination with the actives and/or personal care ingredients described above.

The cosmetic composition may include an antiparasite agent. The antiparasite agent can be of any type. Examples of antiparasite agents include, but are not limited to, hexachlorobenzene, carbamate, naturally occurring pyrethroids, permethrin, allethrin, malathion, piperonyl butoxide, and combinations thereof.

The cosmetic composition may include an antimicrobial agent, also referred to as germicidal agent. The antimicrobial agent can be of any type. Examples of antimicrobial agents include, but are not limited to, phenols, including cresols and resorcinols. Such compositions may be used to treat infections of the skin. An example of a very common skin infection is acne, which involve infestation of the sebaceous gland with *P. acnes*, as well as *Staphylococus auras* or *Pseudomonas*. Examples of useful antiacne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g. cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate and cholate; parachlorometaxylenol; and combinations thereof.

Phenols, in concentrations of about 0.2, 1.0, and 1.3, % by weight, are generally bacteriostatic, bactericidal, and fungicidal, respectively. Several phenol derivatives are more potent than phenol itself, and the most important among these are the halogenated phenols and bis-phenols, the alkyl-substituted phenols and the resorcinols. Hydrophobic antibacterials include triclosan, triclocarbon, eucalyptol, menthol, methylsalicylate, thymol, and combinations thereof.

The cosmetic composition may include an antifungal agent. The antifungal agent can be of any type. Examples of antifungal agents include, but are not limited to, azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and combinations thereof. U.S. Pat. No. 4,352,808 discloses 3-aralkyloxy-2, 3-dihydro-2-(1H-imidazolylmethyl)benzo[b]thiophene compounds having antifungal and antibacterial activity, which is incorporated herein by reference.

The cosmetic composition may include a steroidal anti-inflammatory agent. The steroidal anti-inflammatory agent can be of any type. Examples of steroidal anti-inflammatory agents include, but are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and combinations thereof.

Topical antihistaminic preparations currently available include 1 percent and 2 percent diphenhydramine (Benadryl® and Caladryl®), 5 percent doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines can also be included in the cosmetic composition. Additionally, so-called "natural" anti-inflammatory agents may be useful. For example, candelilla wax, alpha bisabolol, aloe vera, Manjistha (extracted from plants in the genus *Rubia*, particularly *Rubia cordifolia*), and Guggal (extracted from plants in the genus *Commiphora*, particularly *Commiphora mukul*, may be used as an active in the cosmetic composition.

The cosmetic composition may include a non-steroidal anti-inflammatory drug (NSAID). The NSAID can be of any type. Examples of NSAIDs include, but are not limited to, the following NSAID categories: propionic to acid derivatives; acetic acid derivatives; fenamic acid derivatives;

biphenylcarboxylic acid derivatives; and oxicams. Such NSAIDs are described in the U.S. Pat. No. 4,985,459 which is incorporated herein by reference. Further examples include, but are not limited to, acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen, bucloxic acid, and combinations thereof.

The cosmetic composition may include an antioxidant/radical scavenger. The antioxidant can be of any type. Examples of antioxidants include, but are not limited to, ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g. N,N-diethylhydroxylamine, amino-guanidine), sulfhydryl compounds (e.g. glutathione), and dihydroxy fumaric acid and its salts may be used, as well as EDTA, BHT and the like, and combinations thereof.

The cosmetic composition may include an antibiotic. The antibiotic can be of any type. Examples of antibiotics include, but are not limited to, chloramphenicol, tetracyclines, synthetic and semi-synthesic penicillins, beta-lactames, quinolones, fluoroquinolnes, macrolide antibiotics, peptide antibiotics, cyclosporines, erythromycin, clindamycin, and combinations thereof.

The cosmetic composition may include a topical anesthetic. The topical anesthetic can be of any type. Examples of topical anesthetics include, but are not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, phenol, pharmaceutically acceptable salts thereof, and combinations thereof.

The cosmetic composition may include an anti-viral agent. The anti-viral agent can be of any type. Examples of anti-viral agents include, but are not limited to, proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell. In particular, anti-viral agents include, but are not limited to, nucleoside analogs (e.g. zidovudine, acyclovir, acyclovir prodrugs, famciclovir, gangcyclovir, vidarabine, idoxuridine, trifluridine, and ribavirin), n-docosanoll foscarnet, amantadine, rimantadine, saquinavir, indinavir, ritonavir, idoxuridine alpha-interferons and other interferons, AZT, and combinations thereof.

The cosmetic composition may include an anti-cancer drug. The anti-cancer drug can be of any type. Examples of anti-cancer drugs include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin-2 (including recombinant interleukin 2, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; and combinations thereof.

Other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epothilone A; epothilone B; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; U.S. Pat. No. 6,162,432, which is incorporated herein by reference); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MWF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl-lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; zinostatin stimalamer; and combinations thereof.

Additional examples of actives include analgesic agents and antihypertensive agents. Analgesic agents are known in the art and are colloquially referred to as painkillers. The analgesic agent may be selected from any known analgesic agents, and specific examples thereof include paracetamol (acetaminophen), morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine, non-steroidal anti-inflammatory agents, such as salicylates, and opioid agents, such as morphine and oxycodone. Antihypertensive agents are known in the art for treating or reducing hypertension, i.e., high blood pressure. The antihypertensive agent may be selected from any known antihypertensive agents, and specific examples thereof include diuretics, adrenergic receptor antagonists (e.g. beta blockers), benzodiazepines, calcium channel blockers, renin inhibitors, etc.

A typical narcotic antagonist is haloxone. Exemplary antitussive agents include, without limitation, diphenhydramine, guaifenesin, hydromorphone, ephedrine, phenylpropanolamine, theophylline, codeine, noscapine, levopropoxyphene, carbetapentane, chlorpehndianol and benzonatate.

Among the sedatives which may be utilized are, without limitation, chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs are, without limitation, quinidine, propranolol, nifedipine, procaine, dobutamine, digitoxin, phenyloin, sodium nitroprusside, nitroglycerin, verapamil HCl, digoxin, nicardipine HCl, and isosorbide dinitrate.

Antiemetics are illustrated by, without limitation, thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include, without limitation, thyroxine, growth hormone (GH), interstitial cell stimulating hormone (ICSH), follicle-stimulating hormone (FSH), thyrotropic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, the invention is applicable only to those hormones which have molecular weights and stereo configurations which will allow passage through the skin.

Female sex hormones that can be used include, without limitations, estradiol, diethylstilbestrol, conjugated estrogens, estrone, norethindrone, medroxyprogesterone, progesterone, and norgestrel.

Typical male sex hormones that may be utilized may be represented by, without limitation, testosterone, methyltestosterone, and fluoxymesterone.

The cosmetic composition can include the (C) personal care ingredient in various amounts. One of ordinary skill in the art can readily select an appropriate amount based on want or need. Further, one of ordinary skill in the art readily understands how to select at least one of the (C) personal care ingredients for preparing the cosmetic composition in view of the desired application/function thereof. For example, the relative amounts of the components of the cosmetic composition are contingent on the presence or absence of various optional components, along with the desired properties of the cosmetic composition and its end use. One of skill in the art readily understands how to optimize relative amounts of these components.

The cosmetic composition may further include a filler. Examples of fillers include talc, micas, kaolin, zinc or titanium oxides, calcium or magnesium carbonates, magnesium hydrogen carbonate, hydroxyapatite, silica, silica sylilate, starch, lauroyllysine, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms (e.g. zinc stearate, magnesium stearate, lithium stearate, zinc laurate or magnesium myristate), non-expanded synthetic polymer powders (e.g. polyethylene powder, tetrafluoroethylene powder, polyamide powder, PMMA powder, polyurethane powder, etc.), expanded powders and powders from natural organic compounds, such as cereal starches, which may or may not be crosslinked, copolymer microspheres (which may be hollow), polytrap, silicone resin microbeads, and mixtures thereof. The fillers may be surface treated to modify affinity or compatibility with remaining components. The filler may independently have any form, e.g. the filler may independently be plateletshaped, spherical or oblong, irrespective of the crystallographic form (for example lamellar, cubic, hexagonal, orthorhombic, etc.). The filler may also be considered as and encompasses "fibers".

A method of preparing the cosmetic composition is also disclosed. The method comprises combining the (a) branched organosiloxane, the (b) crosslinking agent and the (c) hydrosilylation catalyst. The method further comprises hydrosilylating the (a) branched organosiloxane, the (b) crosslinking agent, and the (c) hydrosilylation catalyst, optionally in the presence of the (B) carrier fluid, to give the (A) silicone elastomer. Finally, the method comprises combining the (A) silicone elastomer with the (B) carrier fluid to give the cosmetic composition.

The components may be combined in any order, optionally under shear or mixing. Parameters associated with reaction conditions may also be controlled, e.g. temperature, pressure, etc. However, the method may be carried out at ambient conditions.

The (A) silicone elastomer may be formed in the presence of the (B) carrier fluid. However, when that is the case, an additional amount of the (B) carrier fluid is typically combined with the (A) silicone elastomer after its preparation to give the cosmetic composition.

In certain embodiments, the cosmetic composition may be a silicone gel, alternatively a silicone organic elastomer gel. In other embodiments, the cosmetic composition may be a silicone elastomer gel paste, alternatively a silicone organic elastomer gel paste. The cosmetic composition may be in the form of a cream, a gel, a paste, a freely pourable liquid, an aerosol, etc. The cosmetic composition may be in the form of monophasic systems, biphasic or alternate multi phasic systems; emulsions, e.g. oil-in-water, water-in-oil, silicone-in-water, water-in-silicone; multiple emulsions, e.g. oil-in-water-in-oil, polyol-in-silicone-in-water, oil-in-water-in-silicone.

In specific embodiments, the cosmetic composition is a gel paste formed by shearing the cosmetic composition. "Shearing", as used herein refers to any shear mixing process, such as obtained from homogenizing, sonalating, or any other mixing processes known in the art as shear mixing. The shear mixing of the cosmetic composition results in a subsequent composition having reduced particle size. The subsequent composition having reduced particle size is then further combined with additional quantities of the (B) carrier fluid. Typically, the amount of carrier fluid added to the subsequent composition to form the gel paste is sufficient to provide a gel paste composition containing from greater than 0 to 30, alternatively from greater than 0 to 20, alternatively from greater than 0 to 10, weight percent of the (A) silicone elastomer based on the total weight of the cosmetic composition.

In embodiments in which the cosmetic composition is in the form of a gel paste, the gel paste may have a viscosity of at least 50, alternatively at least 100, or alternatively at least 200, Pa·s, as measured on a Brookfield DVII+viscometer with Helipath attachment using spindle T-D (20.4 mm crossbar) at 2.5 rpm.

The cosmetic compositions disclosed herein are well suited for a number of end use applications, and a treatment method is additionally provided.

The treatment method comprises applying the cosmetic composition to a substrate. Generally, the substrate comprises a portion of a mammal, particularly a human. One specific example of a suitable substrate is skin. However, the substrate need not be skin or dermis. For example, when the personal care composition comprises the hair care composition, the substrate is typically hair, which is a protein filament that grows from the follicles of skin. Alternatively, when the personal care composition is the nail care composition, the substrate is a nail, which comprises keratin. Alternatively still, when the personal care composition is the tooth care composition, the substrate is at least one tooth.

The step of applying may be carried out via any technique for contacting the substrate with the cosmetic composition. For example, the cosmetic composition may simply be applied to the substrate by a user, e.g. the user supplying the substrate, or by another. The cosmetic composition may be dispensed, spread, and/or applied on the substrate, optionally while applying a force to spread or apply the cosmetic composition. In certain embodiments, the substrate may also take the form of a bandage or similar article. Such articles can thus carry and deliver the cosmetic composition to the user's skin when contacted. Alternatively, the bandage or other article may be at least partially coated with the cosmetic composition, and the substrate is contacted with the cosmetic composition by applying and optionally adhering the bandage or other article including the cosmetic composition to the substrate, e.g. the user's skin. As another example, when the personal care composition comprises the tooth care composition, the tooth care composition may contact the substrate (e.g. teeth) by applying via a brush.

More specifically, when the cosmetic composition comprises the hair care composition, the hair care composition may be used on hair in a conventional manner. An effective amount of the cosmetic composition for washing or conditioning hair is applied to the hair. Such effective amounts generally range from about 1 to about 50, alternatively from about 1 to about 20, grams. Application to the hair typically includes working the cosmetic composition through the hair such that most or all of the hair is contacted with the cosmetic composition. These steps can be repeated as many times as desired to achieve the desired benefit.

Benefits obtained from using the hair care composition on hair include one or more of the following benefits: color retention, improvement in coloration process, hair conditioning, softness, detangling ease, silicone deposition, anti-static, anti-frizz, lubricity, shine, strengthening, viscosity, tactile, wet combing, dry combing, straightening, heat protection, styling, or curl retention.

When the cosmetic composition comprises the skin care composition, the skin care composition may be used on skin in a conventional manner. An effective amount of the cosmetic composition for the purpose is applied to the skin. Such effective amounts generally range from about 1 to about 3, mg/cm$^2$. Application to the skin typically includes working the cosmetic composition onto or into the skin. This method for applying to the skin comprises the steps of contacting the skin with the cosmetic composition in an effective amount and then rubbing the cosmetic composition into the skin. These steps can be repeated as many times as desired to achieve the desired benefit.

Benefits obtained from using the skin care composition on skin include one or more of the following benefits: stability in various formulations (o/w, w/o, anhydrous), utility as an emulsifier, level of hydrophobicity, organic compatibility, substantivity/durability, wash off resistance, interactions with sebum, performance with pigments, pH stability, skin softness, suppleness, moisturization, skin feel, long lasting, long wear, long lasting color uniformity, color enhancement, foam generation, optical effects (soft focus), stabilization of actives.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The following examples are intended to illustrate the current embodiments and are not to be viewed in any way as limiting to the scope of the same.

EXAMPLES

Example 1

A cosmetic composition is prepared in accordance with the subject disclosure. The following components in Table 1 are disposed in a sealed 4 oz sample jar to and heated to 75° C.

TABLE 1

| Component | Amount (g) |
| --- | --- |
| Branched organosiloxane 1 | 0.28 |
| Branched organosiloxane 2 | 5.40 |
| Crosslinking agent 1 | 0.83 |
| Crosslinking agent 2 | 3.7 |
| Carrier fluid 1 | 50 |

Branched organosiloxane 1 is tetra(dimethylvinylsiloxy) silane.

Branched organosiloxane 2 is tetravinyl-terminated dimethyl siloxane silsesquioxane (where subscript c is about 30).

Crosslinking agent 1 is a dimethyl/methyl hydrogen, trimethylsiloxy-terminated siloxane.

Crosslinking agent 2 is dimethyl, hydrogen-terminated siloxane.

Carrier fluid 1 is a cyclosiloxane, D5.

0.09 grams of a platinum hydrosilylation catalyst are disposed in the jar and mixed for a period of time of from 11 to 13 minutes. The jar is paced into an oven at 70° C. to cure and is then cooled to room temperature to give a silicone elastomer gel.

The silicone elastomer gel is subjected to high shear mixing in a Waring® Commercial Laboratory blender.

45.88 grams of the silicone elastomer gel is sheared for 30 seconds at setting 1, then for 30 seconds at setting 2, then for 30 seconds at setting 3. 13.59 grams of the carrier fluid 1 are disposed in the blender, followed by shearing for 30 seconds at setting 1, then for 30 seconds at setting 2, then for 30 seconds at setting 3. Between each setting, material is scraped from the sides of the blender with a spatula and placed back into the bulk. An elastomer gel paste results.

The elastomer gel paste is clear and colorless and has a viscosity of from 300,000 to 350,000 cP at 25° C.

Example 2

Another cosmetic composition is prepared in accordance with the subject disclosure. The following components in Table 2 are disposed in a sealed 16 oz sample jar to and heated to 75° C.

TABLE 2

| Component | Amount (g) |
| --- | --- |
| Branched organosiloxane 1 | 3.6 |
| Crosslinking agent 2 | 38.9 |
| Carrier fluid 1 | 207.5 |

0.48 grams of a platinum hydrosilylation catalyst are disposed in the jar and mixed for a period of time of from 11 to 13 minutes. The jar is paced into an oven at 70° C. to cure and is then cooled to room temperature. The contents of the jar are mixed for 20-25 minutes and again heated in the oven at 70° C. for three hours to give a silicone elastomer gel.

The silicone elastomer gel is subjected to high shear mixing in a Waring® Commercial Laboratory blender.

53.53 grams of the silicone elastomer gel is sheared for 30 seconds at setting 1, then for 30 seconds at setting 2, then for 30 seconds at setting 3. Between each setting, material is scraped from the sides of the blender with a spatula and placed back into the bulk. Then, 15.81 grams of the carrier fluid 1 are disposed in the blender, followed by shearing for 30 seconds at setting 1, then for 30 seconds at setting 2, then for 30 seconds at setting 3 to give an elastomer gel paste.

The elastomer gel paste is clear and colorless and has a viscosity of from 700,000 to 850,000 cP at 25° C.

Example 3

Another cosmetic composition is prepared in accordance with the subject disclosure. The following components in Table 3 are disposed in a sealed 16 oz sample jar to and heated to 70° C.

TABLE 3

| Component | Amount (g) |
| --- | --- |
| Crosslinking agent 2 | 14.8 |
| Crosslinking agent 3 | 23.8 |
| Carrier fluid 1 | 59.9 |

Crosslinking agent 3 is dimethylvinylsiloxy-terminated d/methyl siloxane. Crosslinking agents 2 and 3 first react in the presence of the carrier fluid 1 such that the crosslinking agent ultimately utilized is the reaction product of crosslinking agents 2 and 3. The crosslinking agent includes silicon-bonded hydrogen atoms from the molar excess in crosslinking agent 2 as compared to the unsaturated groups of crosslinking agent 3.

0.28 grams of a platinum hydrosilylation catalyst are disposed in the jar and stirred for 10 minutes to form the reaction product of the crosslinking agents 2 and 3. Then, 1.40 grams of the branched organosiloxane 1 are disposed in the jar and mixed for a period of time of from 50 to 60 minutes. The jar is again sealed and placed in an oven at 70° C. to cure for 4 hours and is then cooled to room temperature to give a silicone elastomer gel.

The silicone elastomer gel is subjected to high shear mixing in a Waring® Commercial Laboratory blender.

36 grams of the silicone elastomer gel is sheared for 30 seconds at setting 1, then for 30 seconds at setting 2, then for 30 seconds at setting 3. Between each setting, material is scraped from the sides of the blender with a spatula and placed back into the bulk. Then, 23.65 grams of the carrier fluid 1 are disposed in the blender, followed by shearing for 30 seconds at setting 1, then for 30 seconds at setting 2, then for 30 seconds at setting 3 to give an elastomer gel paste.

The elastomer gel paste is clear and colorless and has a viscosity of 1,562,708 cP at 25° C.

Example 4

Another cosmetic composition is prepared in accordance with the subject disclosure. The following components in Table 4 are disposed in a sealed 16 oz sample jar to and heated to 70° C.

TABLE 4

| Component | Amount (g) |
| --- | --- |
| Crosslinking agent 2 | 23.41 |
| Crosslinking agent 4 | 14.74 |
| Carrier fluid 1 | 59.88 |

Crosslinking agent 4 is α,ω-bismethallyl polypropylene oxide having about 20 propylene oxide (PO) units. Crosslinking agents 2 and 4 first react in the presence of the carrier fluid 1 such that the crosslinking agent ultimately utilized is the reaction product of crosslinking agents 2 and 4. The crosslinking agent includes silicon-bonded hydrogen atoms from the molar excess in crosslinking agent 2 as compared to the unsaturated groups of crosslinking agent 4.

0.19 grams of a platinum hydrosilylation catalyst are disposed in the jar and stirred for 10 minutes to form the reaction product of the crosslinking agents 2 and 4. Then, 1.77 grams of the branched organosiloxane 1 are disposed in the jar and mixed for a period of time of from 50 to 60 minutes. The jar is again sealed and placed in an oven at 70° C. to cure for 4 hours and is then cooled to room temperature to give a silicone elastomer gel.

The silicone elastomer gel is subjected to high shear mixing in a Waring® Commercial Laboratory blender.

36 grams of the silicone elastomer gel is sheared for 30 seconds at setting 1, then for 30 seconds at setting 2, then for 30 seconds at setting 3. Between each setting, material is scraped from the sides of the blender with a spatula and placed back into the bulk. Then, 23.65 grams of the carrier fluid are disposed in the blender, followed by shearing for 30 seconds at setting 1, then for 30 seconds at setting 2, then for 30 seconds at setting 3 to give an elastomer gel paste.

The elastomer gel paste is clear and colorless and has a viscosity of 1,391,458 cP at 25° C.

Example 5

Another cosmetic composition is prepared in accordance with the subject disclosure. The following components in Table 5 are disposed in a sealed 16 oz sample jar to and heated to 70° C.

TABLE 5

| Component | Amount (g) |
| --- | --- |
| Crosslinking agent 2 | 18 |
| Crosslinking agent 4 | 3.9 |
| Crosslinking agent 5 | 0.35 |
| Carrier fluid 1 | 75.7 |

Crosslinking agent 5 is 1,5-hexadiene, Crosslinking agents 2, 4 and 5 first react in the presence of the carrier fluid 1 such that the crosslinking agent ultimately utilized is the reaction product of crosslinking agents 2, 4 and 5. The crosslinking agent includes silicon-bonded hydrogen atoms from the molar excess utilized as compared to the unsaturated groups.

0.38 grams of a platinum hydrosilylation catalyst are disposed in the jar and stirred for 10 minutes to form the reaction product of the crosslinking agents 2, 4 and 5. Then, 1.7 grams of the branched organosiloxane 1 are disposed in the jar and mixed for a period of time of from 50 to 60 minutes. The jar is again sealed and placed in an oven at 70° C. to cure for 4 hours and is then cooled to room temperature to give a silicone elastomer gel.

The silicone elastomer gel is subjected to high shear mixing in a Waring® Commercial Laboratory blender.

36 grams of the silicone elastomer gel is sheared for 30 seconds at setting 1, then for 30 seconds at setting 2, then for 30 seconds at setting 3. Between each setting, material is scraped from the sides of the blender with a spatula and placed back into the bulk. Then, 16.9 grams of the carrier fluid are disposed in the blender, followed by shearing for 30 seconds at setting 1, then for 30 seconds at setting 2, then for 30 seconds at setting 3 to give an elastomer gel paste.

The elastomer gel paste is clear and colorless and has a viscosity of 1,000,000 cP at 25° C.

The elastomer gel paste of Example 1 is utilized to prepare additional cosmetic compositions.

Cosmetic Composition 1

A bright primer is formed with the elastomer gel paste of Example 1. The bright primer comprises the following components from Table 7 (with the amount being a weight percent based on the total weight of the bright primer).

TABLE 7

| Component | Amount (g) |
| --- | --- |
| PEG-10 dimethicone | 4 |
| Elastomer gel paste | 30 |
| Ethylhexyl methoxycinnamate | 7.5 |
| Glycerin | 21.5 |
| Water | 20 |

The PEG-10 dimethicone, elastomer gel paste, and ethylhexyl methoxycinnamate (a personal care ingredient) are combined to form a Phase A, and the glycerin and water are combined to form a Phase B. Phase A is mixed at a speed of 400 rpm. After matching the reflection index of Phase B and Phase A, Phase B is slowly added to Phase A while mixing until a uniform mixture is obtained, the uniform mixture being the bright primer. The bright primer has an excellent appearance and silky feel to the touch.

Cosmetic Composition 2

A foundation (mousse-like) is formed with the elastomer gel paste of Example 1. The foundation comprises the following components from Table 8 (with the amount being a weight percent based on the total weight of the foundation):

TABLE 7

| Phase | Component | Amount (g) |
| --- | --- | --- |
| A | Dimethicone/vinyl dimethicone crosspolymer (with silica) | 15 |
| A | Dimethicone with zinc oxide | 5 |
| B | Cyclopentasiloxane (D5) | 25 |
| B | Dimethicone/vinyl dimethicone crosspolymer | 4 |
| B | Elastomer gel paste | 25 |
| C | Iron oxide yellow | 0.4 |
| C | Iron oxide red | 0.2 |
| C | Iron oxide black | 0.05 |
| C | Titanium dioxide | 5.35 |
| C | Dimethicone | 20 |

Phase A, Phase B and Phase C are separately formed and mixed to form individual phases prior to preparing the foundation. After Phases A, B and C are prepared and mixed, Phases A, B and C are mixed uniformly to give the foundation, which has an excellent texture and wrinkle masking properties.

Cosmetic Composition 3

An anhydrous primer is formed with the elastomer gel paste of Example 1. The anhydrous primer comprises the following components from Table 8 (with the amount being a weight percent based on the total weight of the anhydrous primer).

TABLE 8

| Component | Amount (g) |
| --- | --- |
| Elastomer gel paste | 65 |
| Cyclopentasiloxane (D5) | 35 |

The elastomer gel paste is mixed at a speed of 400 rpm. The cyclopentasiloxane is slowly added to the elastomer gel paste under mixing until uniform to give the anhydrous primer.

Cosmetic Composition 4

A second anhydrous primer is formed with the elastomer gel paste of Example 1. The second anhydrous primer comprises the following components from Table 9 (with the amount being a weight percent based on the total weight of the second anhydrous primer).

TABLE 9

| Component | Amount (g) |
| --- | --- |
| Elastomer gel paste | 35 |
| Cyclopentasiloxane (D5) | 55 |
| Dimethicone and dimethicone/vinyl dimethicone crosspolymer | 10 |

The elastomer gel paste is mixed at a speed of 400 rpm. The dimethicone and dimethicone/vinyl dimethicone crosspolymer are slowly added to the elastomer gel paste under mixing to give an intermediate mixture. The cyclopentasiloxane is slowly added to the intermediate mixture under mixing until uniform to give the second anhydrous primer.

Cosmetic Composition 5

An emulsion is formed with the elastomer gel paste of Example 1. The emulsion comprises the following components from Table 10 (with the amount being a weight percent based on the total weight of the foundation):

TABLE 10

| Phase | Component | Amount (g) |
| --- | --- | --- |
| A | Pentacyclosiloxane (D5) | 21 |
| A | PEG-12 dimethicone | 4 |
| A | Lauryl PEG/PPG-18/18 methicone | 0.5 |
| B | Elastomer gel paste | 4 |
| C | Deionized water | 30 |
| C | Thickening agent (sodium polyacrylate blend) | 2 |
| D | Deionized water | 42.5 |

Phase A is formed and mixed. Phase B is then disposed in Phase A under high speed stirring. Then, Phase C is formed and incorporated under mixing. Finally, Phase D is also incorporated under mixing to give the resulting emulsion.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

The invention claimed is:

1. A cosmetic composition comprising:
   (A) a silicone elastomer comprising the reaction product of:
   (a) a branched organosiloxane having the following general formula:

wherein each R independently is $R^1$ or a substituted or unsubstituted hydrocarbyl group, and each $R^1$ independently is an unsaturated group or each $R^1$ is a silicon-bonded hydrogen atom;
   (b) a crosslinking agent having an average of at least two functional groups $R^2$ reactive with $R^1$ of the (a) branched organosiloxane; and
   (c) a hydrosilylation catalyst; and
   (B) a carrier fluid;
   with the proviso that when each $R^1$ independently is an unsaturated group, each $R^2$ is a silicon-bonded hydrogen atom; and when each $R^1$ is a silicon-bonded hydrogen atom, each $R^2$ is an unsaturated group.

2. The cosmetic composition of claim 1, further comprising (C) a personal care ingredient.

3. The cosmetic composition of claim 2, wherein said (C) personal care ingredient is further defined as a skin care ingredient.

4. The cosmetic composition of claim 3, wherein said skin care ingredient is selected from the group consisting of water phase stabilizing agents, cosmetic biocides, conditioning agents, emollients, moisturizers, colorants, dyes, ultraviolet (UV) absorbers, sunscreen agents, antiperspirants, antioxidants, fragrances, antimicrobial agents, antibacterial agents, antifungal agents, antiaging actives, anti-acne agents, skin-lightening agents, pigments, preservatives, pH controlling agents, electrolytes, chelating agents, plant extracts, botanical extracts, sebum absorbents, sebum control agents, vitamins, waxes, surfactants, detergents, emulsifiers, thickeners, propellant gases, skin protectors, film-forming polymers, light scattering agents, and combinations thereof.

5. The cosmetic composition of claim 2, wherein said (C) personal care ingredient is further defined as a hair care ingredient.

6. The cosmetic composition of claim 5, wherein said hair care ingredient is selected from the group consisting of conditioning agents, colorants, dyes, ultraviolet (UV) absorbers, preservatives, plant extracts, fatty alcohols, vitamins, fragrance, anti-dandruff agents, color care additives, pearlising agents, pH controlling agents, electrolytes, chelating agents, styling agents, ceramides, amino-acid derivatives, suspending agents, surfactants, detergents, emulsifiers, thickeners, oxidizing agents, reducing agents, film-forming polymers, and combinations thereof.

7. The cosmetic composition of claim 1, wherein each $R^1$ independently is an unsaturated group and each $R^2$ is a silicon-bonded hydrogen atom.

8. The cosmetic composition of claim 1, wherein each $R^1$ is a silicon-bonded hydrogen atom and each $R^2$ independently is an unsaturated group.

9. The cosmetic composition of claim 1, wherein said (a) branched organosiloxane has the following general formula:

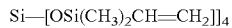
Si—[OSi(CH$_3$)$_2$CH=CH$_2$]$_4$

10. The cosmetic composition of 1, wherein said (b) crosslinking agent is an organosilicon compound.

11. The cosmetic composition of claim 1, wherein said (b) crosslinking agent is an organic compound.

12. The cosmetic composition of claim 1, wherein said (b) crosslinking agent comprises an unsaturated hydrocarbon.

13. The cosmetic composition of claim 12, wherein said unsaturated hydrocarbon comprises an α,ω-diene of the formula CH$_2$=CH(CH$_2$)$_b$CH=CH$_2$, an α,ω-diyne of the formula CH≡C(CH$_2$)$_b$C≡CH, an α,ω-ene-yne of the formula CH$_2$=CH(CH$_2$)$_b$C≡CH, or mixtures thereof, where subscript b independently is from 0 to 20.

14. The cosmetic composition of claim 1, wherein said (b) crosslinking agent comprises a polyoxyalkylene.

15. A method of preparing the cosmetic composition of claim 1, said method comprising:

combining the (a) branched organosiloxane, the (b) crosslinking agent having an average of at least two functional groups R$^2$ reactive with R$^1$ of the (a) branched organosiloxane; and the (c) hydrosilylation catalyst; and hydrosilylating the (a) branched organosiloxane, the (b) crosslinking agent, and the (c) hydrosilylation catalyst, optionally in the presence of the (B) carrier fluid, to give the (A) silicone elastomer; and combining the (A) silicone elastomer with the (B) carrier fluid to give the cosmetic composition.

16. The method of claim 15, further comprising:

combining (C) a personal care ingredient with the (a) branched organosiloxane, the (b) crosslinking agent, and the (c) hydrosilylation catalyst; and/or combining (C) a personal care ingredient with the (A) silicone elastomer and the (B) carrier fluid.

* * * * *